US011051972B1

(12) United States Patent
Buford

(10) Patent No.: US 11,051,972 B1
(45) Date of Patent: *Jul. 6, 2021

(54) NON-INVASIVE, NON-GRAVITATIONALLY DEPENDENT, PRESSURIZED METHOD FOR RAPID RECLAMATION AND VOLUME EXPANSION OF MEDICATION FROM URINE

(71) Applicant: Kevin-Steven Creagh Buford, New Orleans, LA (US)

(72) Inventor: Kevin-Steven Creagh Buford, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/118,196

(22) Filed: Dec. 10, 2020

Related U.S. Application Data

(60) Provisional application No. 62/986,060, filed on Mar. 6, 2020.

(51) Int. Cl.
*A61F 5/451* (2006.01)
*A61J 3/02* (2006.01)
(Continued)

(52) U.S. Cl.
CPC ............. *A61F 5/451* (2013.01); *A61J 3/02* (2013.01); *B01D 61/022* (2013.01); *B01D 61/18* (2013.01); *B01D 63/082* (2013.01); *B01D 2257/70* (2013.01); *B01D 2257/91* (2013.01); *B01D 2315/16* (2013.01)

(58) Field of Classification Search
CPC .......... A61F 5/451; A61J 3/02; B01D 61/022; B01D 61/18; B01D 63/082; B01D 2257/70; B01D 2257/91; B01D 2315/16
See application file for complete search history.

(56) References Cited

U.S. PATENT DOCUMENTS 5,076,933 A    12/1991  Glenn et al.
2002/0035750 A1    3/2002  Braxton
(Continued)

FOREIGN PATENT DOCUMENTS

CN    205803156 U    12/2016
DE        4129041 A1 *  3/1993    ............... C07K 1/36
(Continued)

OTHER PUBLICATIONS

"A Method for the Recovery of Penicillin from Urine", Translational Research, V. 29, Issue 7, pp. 769-771 (1944) (Year: 1944).*
(Continued)

*Primary Examiner* — Dirk R Bass
(74) *Attorney, Agent, or Firm* — McBee Moore & Vanik IP, LLC

(57) ABSTRACT

The present disclosure relates to a non-invasive, non-gravitationally dependent, pressurized method for the rapid selective extraction, volume expansion, and reclamation of medication and medication metabolites (including but not limited to naturally occurring or engineered hormones, chemicals, antibodies, enzymes, lipids, proteins or pharmaceutical products) from urine. The disclosure further relates to methods for reclamation of medication from urine in a pressurized system and methods of using the medication reclaimed from that urine.

13 Claims, 3 Drawing Sheets

(51) Int. Cl.
*B01D 61/02* (2006.01)
*B01D 61/18* (2006.01)
*B01D 63/08* (2006.01)

(56) References Cited

U.S. PATENT DOCUMENTS

| | | | |
|---|---|---|---|
| 2003/0105344 A1* | 6/2003 | Ahnsorge | C07J 1/00 |
| | | | 552/625 |
| 2006/0011545 A1 | 1/2006 | Latza | |
| 2011/0104026 A1 | 5/2011 | Yoon et al. | |
| 2013/0102948 A1 | 4/2013 | Reich et al. | |
| 2014/0042094 A1 | 2/2014 | Montagu et al. | |
| 2014/0231331 A1 | 8/2014 | De Los Reyes et al. | |
| 2015/0050706 A1 | 2/2015 | Buekenhoudt et al. | |
| 2015/0209731 A1 | 7/2015 | Vander Hoff et al. | |

FOREIGN PATENT DOCUMENTS

| | | | |
|---|---|---|---|
| WO | 2000000265 A1 | 1/2000 | |
| WO | 2011067748 A1 | 6/2011 | |

OTHER PUBLICATIONS

PCT International Search Report for PCT/US2020/026006, dated Jun. 29, 2020.
International Search Report for Application No. PCT/US2020/64309 dated Mar. 10, 2021.

* cited by examiner

NON-INVASIVE, NON-GRAVITATIONALLY DEPENDENT, PRESSURIZED METHOD FOR RAPID RECLAMATION AND VOLUME EXPANSION OF MEDICATION FROM URINE

CROSS-REFERENCE TO RELATED APPLICATIONS

This application claims the benefit of U.S. Provisional Application No. 62/986,060, filed 6 Mar. 2020, the contents of which are herein incorporated by reference in their entirety.

This application is related to U.S. application Ser. No. 16/830,056, filed 25 Mar. 2020, and to PCT Application No. PCT/US2020/026006, filed 31 Mar. 2020.

FIELD OF INVENTION

The present disclosure relates to a non-invasive, non-gravitationally dependent, pressurized method for rapid and selective extraction, volume expansion, and reclamation of medication and medication metabolites, including but not limited to naturally occurring or engineered hormones, chemicals, antibodies, enzymes, lipids, proteins or pharmaceutical products from urine.

BACKGROUND OF THE INVENTION

Mankind is on the brink of embarking on voyages for deep-space exploration and potential establishment of off-world colonies and settlements. Basic life-sustaining resources which are abundant on the Earth such as food, water, oxygen and medications are not known to be available in space at this time. Weight and cargo constraints limit the amount of these life-sustaining resources which space explorers can take with them on their voyage. Once they arrive at their interplanetary destination they will be forced to be completely self-reliant, or they will die.

The United States National Aeronautics and Space Administration (NASA) estimates that it will take 6-8 months to travel from the Earth to Mars and the window to travel from Earth to Mars only occurs once every 26 months. If those NASA estimates are accurate, once astronauts arrive on Mars after their two-year journey, they will be forced to self-sustain for approximately 3 years between resupply missions (which could also be delayed or limited due to logistics and expense).

While oxygen, food and water utilization can be carefully calculated, rationed and predicted, it is much more difficult to control and predict antibiotic and rescue medicine requirements. During prolonged colonization missions there is a very real possibility that medications may run out, lost, or damaged and there may be insufficient quantities to treat sick, poisoned, exposed or infected people (e.g., astronauts).

Lack of available supply of medication, inability to import new medications or their critical ingredients, and inability to manufacture new medication will result in increased morbidity and mortality, and may ultimately destroy humanity's hope for interplanetary colonization.

Reclamation of medication from urine may become the only viable option to provide any treatment at all to space explorers. Reclamation from blood would require extensive decontamination/sterilization between individuals and would pose an increased risk of infections, health hazards and complications. Reclamation from stool would be impractical due to infection control and contamination hazards. Reclamation from sweat/tears/saliva would be low yield.

Thus, reclamation of medication and medication metabolites from urine would be essential to successful interplanetary colonization. The disclosed method provides a practical low cost, high-yield solution to this problem.

NASA currently utilizes a method to reclaim drinking water from urine, which addresses the water shortage in space, but said method does not allow for the reclamation of medication. The inventor has developed a platform method utilizing a series of innovative steps, which can be integrated into innumerable water reclamation systems, thereby enabling astronauts to reclaim an abundance of medication from urine based solely on their urinary excretion properties (see chart) without interfering with water reclamation.

During World War II (WW II) Penicillin was difficult to manufacture and in critically short supply. Doctors employed a very time-consuming and complex 21-stage, drug specific, chemical process to recover penicillin from urine during that time of crisis and used it to treat additional patients. The method was published in a medical journal and implemented in military facilities during WW II [15].

This 21-step method was time consuming, very technical, laborious and required a fully functional lab, complete with supplies, reagents and highly trained staff. The time-consuming and complex 21-step chemical method was drug specific to penicillin and would not work to recover any other medications from urine.

Since WW II, we have had world-wide advances in various fields of science and technology. Factory production of medication coupled with their ease of availability have made the thought of reclaiming medication seemingly irrelevant. Deep-space exploration and potential establishment of off-world colonies and settlements requires practical solutions to problems that we don't currently face on Earth.

BRIEF SUMMARY

The present disclosure relates generally to the selective extraction and rapid recycling of medication from urines (at least one urine) using a Pressurized Filtration System. In an embodiment, the method to extract and/or recycle at least one medication from at least one urine comprises:
(a) Collecting at least one urine (non-limiting examples include tears, sweat, saliva, urine, blood, and feces/tissue, which can be liquified, from a subject, preferably but not limited to an animal or mammal, and more preferably a human mammal);
(b) Processing at least one urine (e.g., grinding, liquefying, optionally blending, adding chemical/reagents, e.g., anticoagulants);
(c) Depositing said processed urine into a filtration system;
(d) Pressurizing the filtration system (>760 mm Hg at 1 Atmosphere Absolute (ATA)) such that the aforementioned processed urine is forced through a mesh barrier or filter of the filtration system, wherein bacteria/cells, or other large contaminants in said processed urine are blocked from further entering the system beyond the mesh barrier or filter;
(e) Wherein the pressurized filtration system (>760 mm Hg at 1ATA) propels the filtrate from said processed urine past the mesh or filter to a nanofilter, forward osmosis filter, or reverse osmosis filter, whereby toxins, and liquid waste remaining in the filtrate are forced through the nanofilter, forward osmosis filter, or reverse osmosis filter (and thereby expelled system) while the medication is trapped in or on the mesh or filter. The trapped medication is simultaneously dried by a constant stream of pressurized air or gas in the system.

(f) Collecting the dried medication from the pressurized filtration system for processing, or storing or potential reuse.

In an embodiment, the present disclosure relates to a non-invasive, non-gravitationally dependent, pressurized method for rapid and selective extraction, reclamation and volume expansion of medication from urine. In an embodiment, the method to reclaim at least one medication from urine comprises:

(a) Collecting urine from a subject or from multiple subjects (and, if from multiple subjects the urine may be pooled), preferably but not limited to an animal or mammal, and more preferably a human mammal);

(b) Depositing said urine into a non-gravitationally dependent filtration system;

(c) Pressurizing said non-gravitationally dependent filtration system such that the aforementioned urine is forced through a mesh barrier or filter of said filtration system, wherein bacteria/cells, or other large contaminants in said urine are blocked from further entering the system beyond the mesh barrier or filter;

(d) Wherein said pressurized filtration system propels the filtrate from said urine past the mesh or filter to a nanofilter, forward osmosis filter, or reverse osmosis filter, whereby toxins, and liquid waste remaining in the filtrate are forced through the nanofilter, forward osmosis filter, or reverse osmosis filter (and thereby expelled from said system as liquid effluent) while the medication is trapped in or on the mesh or filter. The trapped medication can be removed from the system for further processing, storing, or potential reuse; and (e) The liquid effluent can then be further processed by a separate system (e.g by a system to reclaim water from effluent), stored, or discarded.

The present disclosure also relates to an innovative method for the reclamation of medication(s) from urine via a non-gravitationally dependent, pressurized method which can be used with minimal equipment, and minimal user training.

In an embodiment, the method comprises a system which can be pressurized.

In an embodiment, non-limiting examples of sources of pressurization include a compressed air or gas tank, pump, motor, or compressor of any kind including but not limited to human-powered, mechanical, electrical, hydraulic or pneumatic.

In an embodiment, said system is non-gravitationally dependent and instead utilizes pressure (which does not rely on gravity) to force the movement of urine across mesh or filters.

In an embodiment, the system comprises a first mesh or filter (or filtration system) configured to prevent the passage (flow-through) of components in animal or mammalian urine that have a size greater than about 150, about 200, about 250, about 300, about 350, about 400, about 450, about 500, about 550, about 600, about 650, about 700, about 750, about 800, about 850, about 900, or about 950 Daltons (Da), about 1, about 2, about 3, about 4, about 5, about 10, about 20, about 30, about 40, about 50, about 60, about 70, about 80, about 90, about 100, about 125, about 150, about 175, about 200, about 225, about 250, about 275, about 300, about 325, about 350, about 375, about 400, about 425, about 450, about 475, or about 500 kilodaltons (kDa), while letting smaller components flow through. The system further comprises a second mesh or filter (or filtration system) configured to allow a liquid (e.g., water, or effluent from the first mesh or filter) to flow through while preventing molecules and medications dissolved in the liquid from flowing through.

In an embodiment, the first mesh or filter comprises a microfiltration system, wherein the first mesh or filter is configured to prevent passage of urine components selected from the group consisting of cells, bacteria, enzymes, suspended solids, and combinations thereof. In an embodiment, the first mesh or filter has a pore size smaller than 0.02 micron ($\mu$m) to exclude the smallest bacteria. Non-limiting examples of an appropriate sized first mesh or filter include: Sterlitech 0.01 micron PCT00162x22100 polycarbonate microfilter.

In an embodiment, the first mesh or filter comprises an ultrafiltration system, wherein the ultrafiltration system is configured to prevent passage of urine components selected from the group consisting of suspended solids, bacteria, cells, fats, enzymes, oils, viruses, proteins, macromolecules, and combinations thereof. In an embodiment, the first mesh or filter has a pore size smaller than 0.02 micron ($\mu$m) to exclude the smallest bacteria. Non-limiting examples Neo-Pure TL3 ultrafiltration purifier, Wheelton PVDF ultrafiltration water purifier, with 0.01 micron filtration or Geekpure advanced ultrafiltration (UF) water purifier with 0.01 micron filtration.

In an embodiment, the first mesh or filter comprises a nanofiltration system wherein the nanofiltration system is configured to prevent passage of urine components selected from the group consisting of viruses, proteins, macromolecules, bacteria, fat, enzymes, suspended solids, and combinations thereof. In an embodiment, the first mesh or filter has a pore size smaller than 0.02 micron ($\mu$m) to exclude the smallest bacteria. Non-limiting examples includes AlkaPlus 0.02 micron nanofilter PLU 19761 and Synder NFG 600-800 Da filter.

In an embodiment, the first mesh or filter comprises a microfiltration system and an ultrafiltration system. In an embodiment, the first mesh or filter comprises a microfiltration system and a nanofiltration system. In an embodiment, the first mesh or filter comprises an ultrafiltration system and a nanofiltration system. In an embodiment, the first mesh or filter comprises a microfiltration system, an ultrafiltration system, and a nanofiltration system.

In an embodiment, urine is applied to the first mesh/filter or filtration system.

In an embodiment, the first mesh or filter comprises a microfiltration system, and the urine applied to the first mesh or filter is first applied to the microfiltration system.

In an embodiment, the first mesh or filter comprises an ultrafiltration system, and the urine applied to the first mesh or filter is first applied to the ultrafiltration system.

In an embodiment, the first mesh or filter comprises a nanofiltration system, and the urine applied to the first mesh or filter is first applied to the nanofiltration system.

In an embodiment, the first mesh or filter comprises a microfiltration system and an ultrafiltration system, and the urine applied to the first mesh or filter is first applied to the microfiltration system and the effluent from the microfiltration system is applied to the ultrafiltration system.

In an embodiment, the first mesh or filter comprises a microfiltration system and a nanofiltration system, and the urine applied to the first mesh or filter is first applied to the microfiltration system and the effluent from the microfiltration system is applied to the nanofiltration system.

In an embodiment, the first mesh or filter comprises an ultrafiltration system and a nanofiltration system, and the urine applied to the first mesh or filter is first applied to the ultrafiltration system and the effluent from the ultrafiltration system is applied to the nanofiltration system.

In an embodiment, the first mesh or filter comprises a microfiltration system, an ultrafiltration system, and a nanofiltration system, and the urine applied to the first mesh or filter is first applied to the microfiltration system, the effluent from the microfiltration system is applied to the ultrafiltration system, and the effluent from the ultrafiltration system is applied to the nanofiltration system.

In an embodiment, the second mesh or filter comprises a reverse osmosis filtration system, wherein the reverse osmosis filtration system is configured to drive a liquid (e.g., water, or effluent from the first filter) through the mesh or filter (membrane) and away from molecules (medications) dissolved in the liquid. Nonlimiting examples of a reverse osmosis Dupont Quick Twist Reverse Osmosis Membrane WFROM1000X 0.001 micron Reverse Osmosis Filter.

In an embodiment, the second filter comprises a mesh or nanofilter wherein the mesh or nanofilter is configured to drive a liquid (e.g., water, or effluent from the first mesh or filter) through the mesh or filter (membrane) and away from molecules (medications) dissolved in the liquid. Nonlimiting examples include: Synder NFW 300-500 Da nanofilter and the Purepro NF270-1812-300 0.0008 micron nanofilter.

In an embodiment, the second mesh or filter comprises a forward osmosis filtration system, wherein the forward osmosis filtration system is configured to drive a liquid (e.g., water, or effluent from the first mesh or filter) through the mesh or filter (membrane) and away from molecules (medications) dissolved in the liquid. Nonlimiting examples of a forward osmosis filter is the Fluid Technology Solutions forward osmosis 0.0007 micron Rainstick water filter.

In an embodiment, effluent from an embodiment of the first mesh/filter is applied to an embodiment of the second mesh/filter or filtration system.

In an embodiment, the urine is from a single mammal or collected from multiple mammals. In an embodiment, the mammals are of the same species or different species. In an embodiment, the mammal(s) is/are human(s) (*Homo sapiens*). In an embodiment, the mammals are all taking the same pharmaceutical compound or combination of pharmaceutical compounds, administered to the mammals by any route, including but not limited to oral, rectal, nasal, topical (including buccal and sublingual), transvaginal, and parenteral (including subcutaneous, intramuscular, intravenous, percutaneous, subdural, and intradural).

In an embodiment, the pressurized filtration system uses pressure to force urine past a mesh/filters or series of meshes/filters, and the urine is filtered through a filtration process comprising multi-stage filtration system connecting a mesh, microfiltration system, ultrafiltration system, reverse osmosis, forward osmosis and/or nanofiltration system to a mesh, microfiltration system, ultrafiltration system, reverse osmosis, forward osmosis and/or nanofiltration system under pressure with the purpose of reclaiming medications or chemicals from urine of subjects treated with or containing at least one pharmaceutical compound in order to potentially treat additional exposed, sick, or infected subjects. This method of reclaiming medication(s) would also prevent medication from being non-selectively extracted, along with other contaminants, and discarded or otherwise being wasted.

In an embodiment, the medication is contained in urine an unchanged, active, inactive or recoverable form in clinically significant amounts. In an embodiment, the subject from which urine is collected from is a human only on the desired medication to be collected. In an embodiment the subject from which urine is collected from is on multiple medications, but the non-desired medications are either not contained in urine or are not recovered in that urine in active form, and/or can be processed/separated out from the desired medication or medications.

In an embodiment, some of these potentially life-saving medications contained in urine include but are not limited to: antibiotics, antivirals, antifungals, steroids, vitamins, antimicrobial, antiparasitic, proteins or any other medications, supplements, or treatments which have been developed or will be developed which are contained in urine in an unchanged, active, inactive or recoverable form in clinically significant amounts. In other words, the instant disclosure is not limited to the foregoing categories of medications, and a skilled artisan will recognize that any and all medications present in urine in an unchanged active or inactive form may be recovered by practicing the disclosed methods or by using the disclosed system.

Tamiflu, Relenza and Rapivab are antiviral medications with a good track record of successfully treating the flu. They are currently being tested to see if they are effective against the novel coronavirus (COVID-19). Levaquin is an antibiotic used to treat severe hospital acquired pneumonia and several kinds of bioterrorism including inhaled anthrax, and the plague. Chloroquin is an antimalarial drug with some antiviral properties. A recent scientific journal article stated that Chloroquin was found to be effective against the novel coronavirus (COVID-19) in a mutli-center study in China [14, 20]. Ciprofloxacin is an antibiotic used to treat several kinds of bioterrorism including anthrax, the plague, life-threatening meningitis and tularemia. The NIH has announced that antiviral medication Remdesivir has been effective against coronavirus in monkeys and clinical trials in humans have begun [17,18, 20]. The antiretroviral drug Kaletra (Ritonavir/Lopinavir) is very effective against HIV and currently being tested against COVID-19. Whereby, aforementioned medications are non-limiting examples of medications contained in urine that can be potentially reclaimed by this novel method.

In an embodiment, the pressurized filtration method is useful for collecting/reclaiming medication from urine for potential treatment of diseases and conditions. A further embodiment provides for a method of treating diseases and conditions comprised of applying the medication collected from the pressurized filtration system discussed in any one of the preceding paragraphs to a subject in need thereof. In a further embodiment, the disease and or condition is caused by a naturally occurring or engineered bacterial or viral infection, bioterrorism pathogen, poison, exposure, extraterrestrial agent, or toxin.

In an embodiment, the disease can be caused by naturally occurring or engineered bacteria, viruses, fungi, poisons, exposures, extraterrestrial agents, toxins or a bioterrorism pathogen. Bioterrorism pathogens are bacteria, viruses, poisons, exposures and toxins that are deliberately scattered in the environment causing human or animal disease or death. Bioterror pathogens include, but are not limited to, anthrax (anthrax), plague (pesto), ulcers (pox), tick-borne encephalitis virus (TBEV) (tick-borne encephalitis) and Ebola virus (Ebola). Bioterror pathogens can also include biotoxins, which are toxins produced by certain organisms. Examples of biotoxins include botulinum toxin produced by *Clostridium botulinum* and ricin isolated from castor bean seeds.

In an embodiment, the medication collected from urine using the pressurized filtration method discussed above, or pharmaceutically acceptable salts and solvates thereof, is used in the preparation of a medicament or pharmaceutical composition to be potentially applied to a subject in need thereof.

The pharmaceutical compositions prepared from the medication collected from urine can be in any form known to those of skill in the art. For instance, in some embodiments the pharmaceutical compositions are in a form of a product for enteral delivery, non-limiting examples include concentrate, dried powder, liquid, capsule, pellet, gel, and pill. In other embodiments, the pharmaceutical compositions of the disclosure are in the form of a product for parenteral administration including but not limited to intranasal, sublingual, auricular, ophthalmic, topical, inhalational, intravenous, intradermal, intramuscular, and subcutaneous administration. The pharmaceutical compositions disclosed herein may also further comprise carriers, binders, diluents, and excipients.

In an embodiment, said medication collected from urine can be purified until it has a purity of ≥75%, ≥80%, ≥85%, ≥90%, ≥95%, ≥96%, ≥97%, ≥98%, or ≥99%. In an embodiment, a pharmaceutical composition is provided comprising the medication collected and purified from urine, either alone or in combination with at least one additional therapeutic agent, with a pharmaceutically acceptable carrier; and uses of the medication or pharmaceutical composition, either alone or in combination with at least one additional therapeutic agent, in the treatment of diseases and/or condition at any stage of the disease or condition. The methods for treating a clinical indication by the pharmaceutical composition disclosed herein, may be effectuated by administering a therapeutically effective amount of the pharmaceutical composition to a subject in need thereof, this therapeutically effective amount may comprise administration of the prodrug to the subject at 1 mg/kg/day, 2 mg/kg/day, 3 mg/kg/day, 4 mg/kg/day, 5 mg/kg/day, 10 mg/kg/day and 20 mg/kg/day. Alternatively, amounts ranging from about 0.001 mg/kg/day to about 0.01 mg/kg/day, or about 0.01 mg/kg/day to about 0.1 mg/kg/day, or about 0.1 mg/kg/day to about 1 mg/kg/day, or about 1 mg/kg/day to 10 mg/kg/day, about 10 mg/kg/day to about 100 mg/kg/day or in any clinically effective dose are also contemplated.

One aspect of the present disclosure is the medication collected and purified from urine disclosed herein as well as the intermediates as used for their synthesis.

The instant disclosure relates to the following enumerated embodiments.

1. A non-invasive, non-gravitationally dependent, pressurized filtration method to selectively reclaim at least one medication from urine, comprising: (a) collecting urine from at least one subject; (b) passing said urine through a non-gravitationally dependent pressurized filtration system, wherein the bacteria/cells, contaminants, toxins, and liquid waste are removed/separated by the pressurized filtration system, and the at least one medication is trapped in the pressurized filtration system; and (c) collecting the at least one medication from the pressurized filtration system.

2. The method of embodiment 1, wherein the pressurized filtration system comprises: (i) a source of pressurization with air or compressed gas; (ii) a first mesh or filter; (iii) a second mesh or filter; and (iv) a source of pressurized air or gas configured to propel urine through the first and second mesh or filter.

3. The method of embodiment 2, wherein (b) comprises passing said urine through the first mesh or filter, and directing the effluent from the first mesh or filter through the second mesh or filter, wherein the at least one medication is retained by the second mesh or filter while the liquid or liquid waste passes through the second mesh filter as effluent.

4. The method of any one of embodiments 2-3, wherein the pressurized filtration method is integrated into a further system, thereby enabling said further system to gain the functionality of reclaiming at least one medication from urine, without interfering with the original function(s) of the further system.

5. The method according to any one of embodiments 2-4, wherein the effluent which passes through the second mesh or filter is further processed or stored.

6. The method of any one of embodiments 2-5, wherein the first mesh or filter and the second mesh or filter are in fluid connection to one another as a single unit or via a connector.

7. The method of any one of embodiments 2-6, wherein the first mesh or filter is configured to prevent the passage of components in urine that have a size greater than about 800 Da while permitting passage of smaller components, and the second mesh or filter is configured to allow passage of effluent from the first mesh or filter while preventing passage of the at least one medication dissolved in the effluent.

8. The method of any one of embodiments 2-7, wherein: (a) the first mesh or filter comprises at least one mesh or filter selected from the group consisting of a microfiltration system, an ultrafiltration system, mesh, reverse osmosis, forward osmosis, and a nanofiltration system, and is configured to prevent passage of urine components selected from the group consisting of suspended solids, bacteria, cells, fats, enzymes, oils, viruses, proteins, macromolecules, and combinations thereof; and (b) the second mesh or filter comprises at least one mesh or filter selected from the group consisting of reverse osmosis filtration system, forward osmosis system and a nanofiltration system, wherein the reverse osmosis filtration, forward osmosis filtration system and/or nanofiltration system is configured such that pressurization of the system propels the urine to pass through the second mesh or filter as effluent while trapping the at least one medication in or on the second mesh or filter.

9. The method of any one of embodiments 1-8, wherein the urine is from a mammal.

10. The method of any one of embodiments 1-9, wherein the at least one subject: (a) is taking only one medication; or (b) is taking multiple medications, but the medications not being recovered are either not excreted in urine, are not recovered from urine in active form, and/or can be separated/processed out from a desired medication.

11. The method of any one of embodiments 1-10, wherein the at least one medication is selected from the group consisting of: antibiotics; antivirals; antifungals; steroids; antimicrobial; antiparasitic; vitamins; proteins; and supplements; wherein the at least one medication is contained in the urine in an unchanged, active, inactive, or recoverable form in clinically significant amounts.

12. The method of any one of embodiments 1-11, further comprising testing the medication reclaimed from the pressurized filtration system for purity or concentration, optionally sterilizing the medication, and optionally reusing or storing the medication.

13. A pharmaceutical composition comprising the medication collected according to any one of embodiments 1-12.

14. A method of treating a disease and/or condition, comprising administering a therapeutically effective amount of the pharmaceutical composition of claim 13 to a subject in need thereof.

15. The method according to claim 14, wherein the disease and/or condition is caused by a naturally occurring or engineered bacterial or viral infection, bioterror pathogen, poison, extraterrestrial agent, exposure or a toxin.

16. The method according to any one of embodiments 1-15, wherein the at least one medication comprises naturally occurring or engineered hormones, chemicals, antibodies, lipids, proteins, enzymes, or pharmaceutical products.

While certain features of this invention shown and described below are pointed out in the annexed claims, the invention is not intended to be limited to the details specified, since a person of ordinary skill in the relevant art will understand that various omissions, modifications, substitutions, and changes in the forms and details of the invention illustrated and in its operation may be made without departing in any way from the spirit of the present invention. No feature of the invention is critical or essential unless it is expressly stated as being "critical" or "essential."

These and other features, aspects, and advantages of embodiments of the present disclosure will become better understood with regard to the following descriptions, claims, and accompanying drawings explained below.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

In an embodiment, a method is provided to reclaim medications from urines. In an embodiment, the method is accomplished through the use of pressurized filtration with the specific purpose reclaiming medications from urine (see, e.g., FIG. 1).

The disclosed pressurized filtration method relies on the scientific certainty that human cells i.e. red/white/epithelial etc. (which can sometimes be found in urine as contaminants) and bacteria are very large, and the main components and toxins in urine are very small. In the chart below I have included the main toxins from urine as an example to demonstrate this. As evidenced by their molecular weights/diameters (ammonia, NaCl, Urea, Creatinine, CaOx, Uric Acid and H2O) are approximately ⅓ the size of the medications. Urobilin gives urine it's color, is in a very low amount in urine and not particularly toxic. By comparison, medications (such as Tamiflu, Chloroquin, Relenza, Levaquin, Rapivab and Ciprofloxacin) are significantly larger than the size of the toxins contained in urine, but are orders of magnitude smaller than bacteria, red blood cells, and white blood cells (TABLE 1).

TABLE 1

Sizes and densities of average toxins in urine, compared to medications

| Chemical | Mol Wt (g/mol) | Density (g/cm$^3$) | Spherical Dia (nm) | % Excreted Unchanged or Active Metabolite in Urine |
|---|---|---|---|---|
| Ammonia | 17.031 | 0.88 | 0.394 | |
| Salt (NaCl) | 58.44 | 2.16 | 0.441 | |
| Urea | 60.06 | 1.32 | 0.525 | |
| Creatinine | 113.12 | 1.09 | 0.69 | |
| Calcium Oxalate | 128.097 | 2.12 | 0.577 | |
| Uric Acid | 168.1103 | 1.87 | 0.658 | |
| Urobilin (low amt) | 590.71 | 1.32 | 1.12 | |
| Water (H2O) | 18.015 | 1 | 0.385 | |
| Tamiflu | 410.4 | 1.08 | 1.064 | 90 |
| Chloroquine | 319.872 | 1.1 | 0.973 | 70 |
| Relenza | 332.31 | 1.75 | 0.844 | 90 |
| Levaquin | 361.368 | 1.5 | 0.914 | 85 |
| Rapivab | 328.407 | 1.4 | 0.906 | 90 |
| Ciprofloxacin HCl | 385.82 | 1.46 | 0.943 | 45 |
| Remdesevir | 602.576 | 1.5 | 1.084 | 60 |

Figure 1:
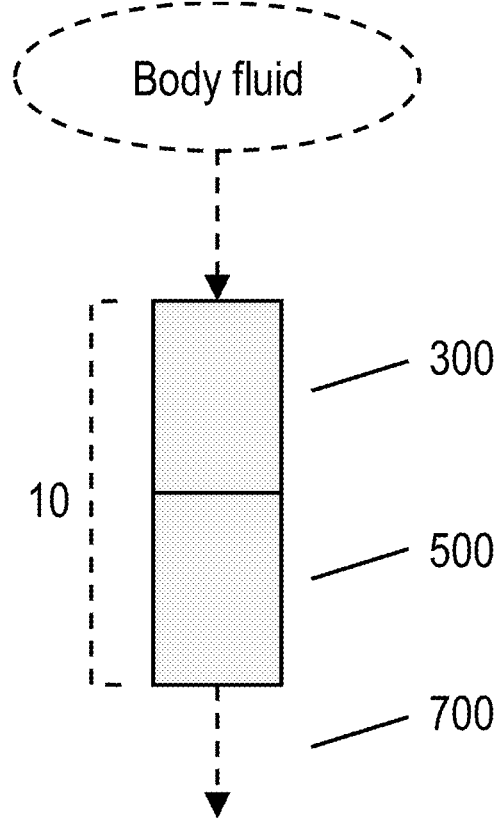
FIG. 1 is a schematic diagram of an embodiment of the pressurized filtration system of the instant disclosure.
Figure 2:
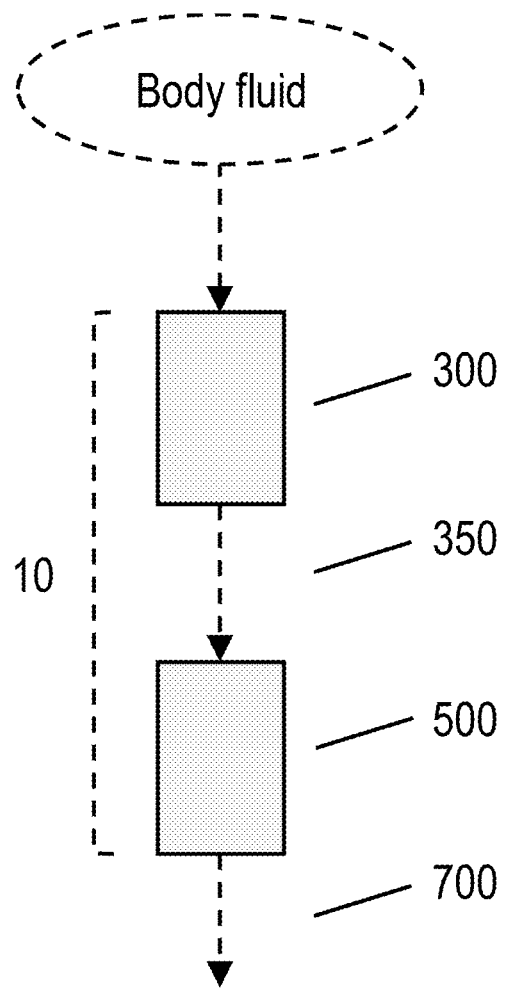
FIG. 2 is a schematic diagram of an embodiment of the pressurized filtration system of the instant disclosure.

In an embodiment the non-gravitationally dependent pressurized filtration method to reclaim medication from urine (10) comprises a source of pressure (30), a first mesh or filter (300) to block bacteria and cells, and a second mesh or filter (500) configured to allow all of the toxins and liquid (700) to pass through the second mesh or filter (500) while leaving dissolved molecules (i.e., the desired medication) behind in or on the second mesh or filter (see FIGS. 1 & 2).

Figure 3:
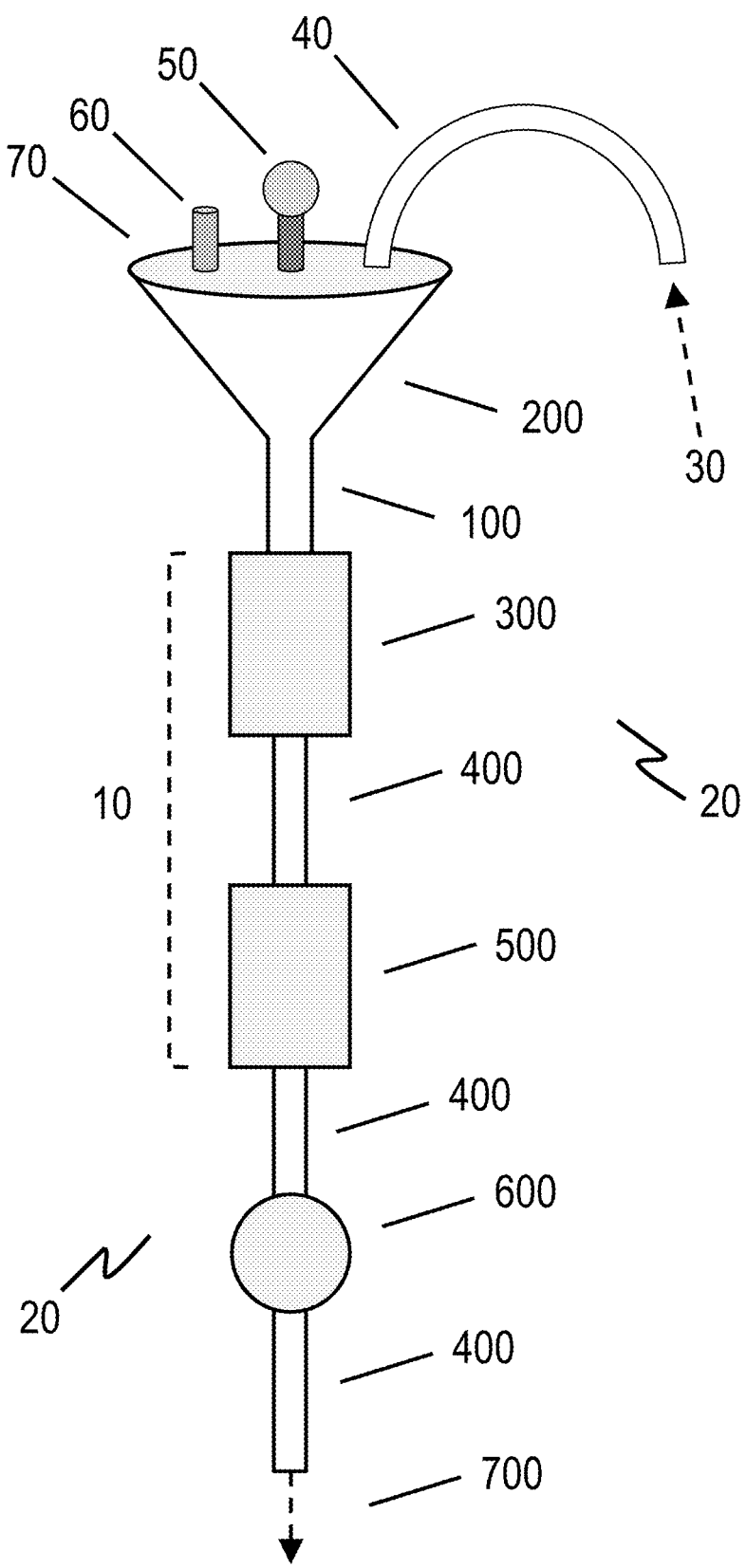
FIG. 3 shows an embodiment of a pressurized filtration system and device discussed herein to collect medication from body fluid.

In an embodiment, the first mesh or filter (300) and the second mesh or filter (500) are in fluid connection to one another as a single unit (see FIG. 1). In an embodiment, the first mesh or filter (300) and the second mesh or filter (500) are in fluid connection to one another via a connector (400). In an embodiment, the connector (400) is tubing (see FIG. 3).

Figure 4:
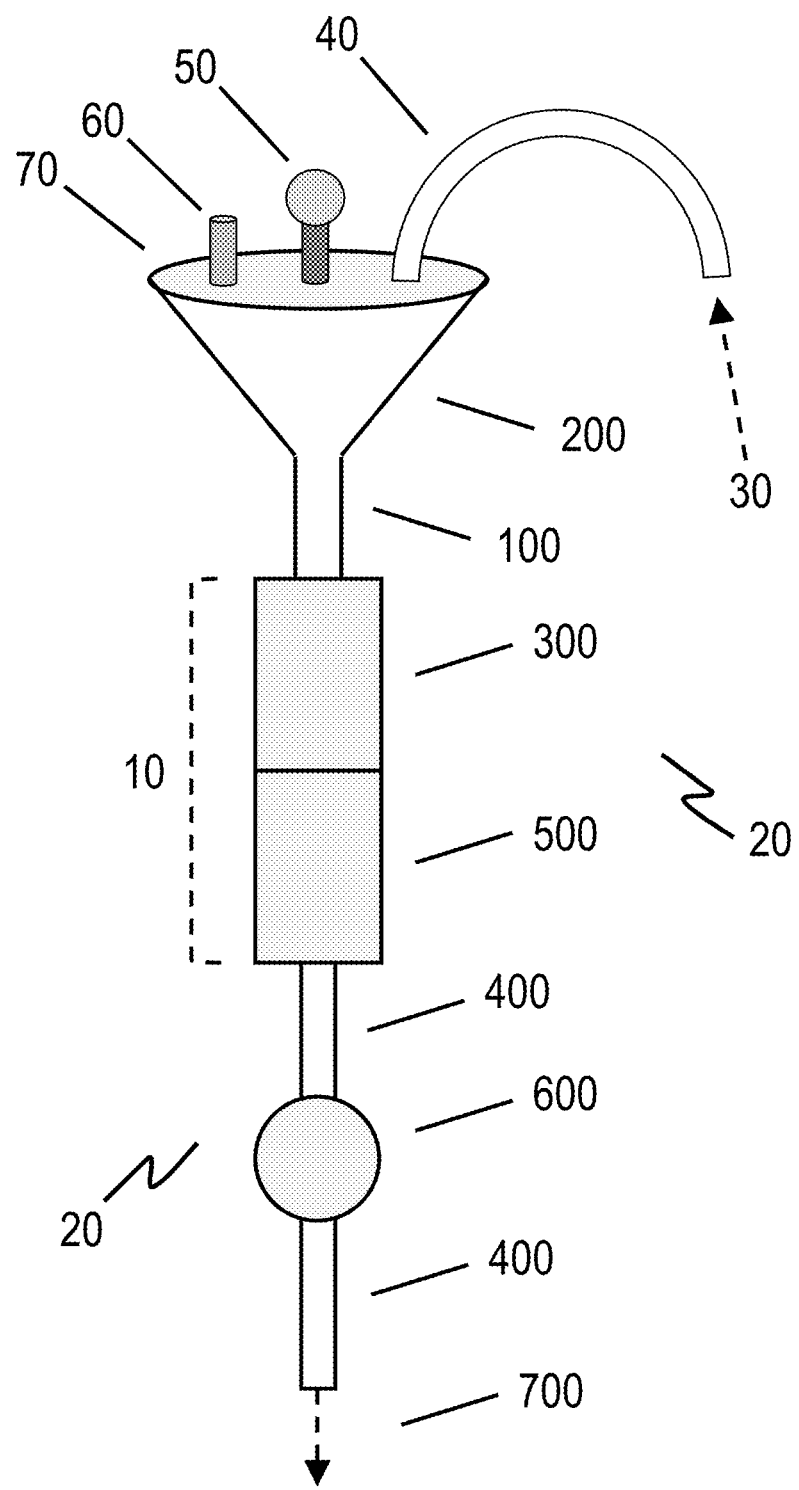
FIG. 4 shows an embodiment of a pressurized filtration system and device discussed herein to collect medication from body fluid.

In an embodiment the non-gravitationally dependent pressurized filtration method to reclaim medication from urine (10) can be integrated into another device or system (such as a device or system used to convert urine to drinking water) in order to enable that device to reclaim both water and medication instead of water alone. This is accomplished by including a series of additional steps wherein a first mesh or filter (300) blocks bacteria and cells, and a second mesh or filter (500) is configured to allow all of the toxins and liquid (700) to pass through while leaving dissolved molecules (i.e. the desired medication(s)) behind (see FIGS. 3 & 4). The first mesh or filter (300) and the second mesh or filter (500) may be in fluid connection to one another as a single unit (FIG. 4) or may be in fluid connection to one another via a connector (400), as in FIG. 3, which may be tubing.

There are numerous advantages and benefits to using the non-gravitationally dependent, pressurized method to reclaim medication from urine, discussed herein, as opposed to the previously discussed 21-stage drug-specific (i.e., only works for Penicillin) complex chemical process which was utilized during WW II to reclaim Penicillin from urine, the advantages including:

- Cost effectiveness: meshes and filters are cheap and can be cleaned/reused. They don't need to be sterile because medication can be processed after recovery to be sterilized if needed.
- Expediency: this is a much faster process than had previously been considered.
- Rapid deployment: this system/method could be deployed across the world in hours
- Comparatively easy to use and requires minimal training.
- Self-contained unit, complex lab equipment is not needed to perform the extraction
- Does not rely on mixing dangerous acids/bases to perform extraction, which puts people at risk for injury
- Can be used to selectively recover various existing and future developed medications rather than specific only to Penicillin The non-invasive, non-gravitationally dependent, pressurized, method described here is a dramatic innovation over a previously described theoretical rudimentary process described in a 1991 German patent (DE4129041), which cannot be integrated into systems to reclaim water from urine. Their method begins with "reducing the volume" of feces, urine or blood containing "valuable substances" (which already renders the method useless for water reclamation). Another step in said German method states that their fractional excretions are subjected to chromatographic concentrating processes (the instant process does not include chromatography and it's not practical to require chromatography in Space). Their method was never put into practice, most likely due to the fact that as described, it was not a fully functioning process due to practical obstacles to implementation, expense, and lack of real-world applicability. This realization would have been obvious to those skilled in the art.

While some meshes or filters do exist that have chemical properties/charges, the typical mesh or filter removes materials based only on size. The pressurized filtering system used depends on the types of mesh or filters available. In an embodiment, the subject from which urine is collected to reclaim medication is a young healthy subject, who is only on the medication to be reclaimed. However, as many drugs are not contained in urine in an active form and drug processing is possible, subjects on multiple medications can also be candidates for this process. In an embodiment, the subject from which the urine is collected to reclaim medication is a subject on multiple medications, wherein the non-desired medications are either not contained in that particular urine in an active form and/or can be processed out from the desired medication to be reclaimed.

The present disclosure also provides methods for reclaiming medication from urine (see FIGS. 3 & 4), comprising:

- Collecting urine containing a medication from suitable patients;
- Depositing the collected urine into a suitable device (non-limiting examples include devices aimed at reclaiming water from urine);
- Forcing the collected urine through a first mesh or filter (300) under pressure, thereby removing bacteria/cells and large contaminants;
- Propelling the effluent from the first mesh filter (300) under pressure (30) through a second mesh or filter (500), wherein the medication is retained in or on the second mesh or filter (500) while the liquid passes through the second mesh or filter (500) as effluent (700); and
- Further processing, storing, or discarding said effluent.

The medication is then reclaimed from the second mesh or filter (500) and processed (tested for purity/concentration, and sterilized if needed) and potentially stored/stockpiled or used to treat the same or additional exposed, sick, or infected subjects.

A further embodiment provides for a method of reclaiming medicine for stockpiling or for treating diseases and conditions comprising applying the (purified) medicine reclaimed from a pressurized filtration system discussed in any one of the preceding paragraphs to a subject in need thereof.

In an embodiment, the medications to be reclaimed from urine comprises any medication which is contained in clinically significant amounts in an unchanged, active, inactive and recoverable form in urine, and are amenable to reclamation using the instant method. In a further embodiment, the medications include but are not limited to: Tamiflu [8], Relenza [9], Rapivab [10,21], Levaquin [11], Chloroquin [12,14], Ciprofloxacin [13], Remdesivir [15], Ritonivir/Lopinivir [16].

In a further embodiment, the term medications includes medications that currently exist or will be developed or discovered for the treatment of exposed, sick, or infected subjects.

In a further embodiment, the term medication includes naturally occurring or engineered hormones, chemicals, antibodies, lipids, enzymes, proteins or products which currently exist or will be developed for the intended stockpile or treatment of deficient, exposed, sick, or infected subjects that can be reclaimed from urine in an unchanged, active, inactive and recoverable form.

In an embodiment, the medications collected from urine according to the disclosure are isolated and purified in a manner known per se, e.g., by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present disclosure which possess a sufficiently basic or acidic functionality, may result in the formation of a salt, such as, in the case of a compound of the present disclosure which is sufficiently basic, a trifluoroacetate or formate salt for example, or, in the case of a compound of the present disclosure which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present disclosure may not fully remove traces of co-solvents, especially such as formic acid or trifluoroacetic acid, to give solvates or inclusion complexes. The person skilled in the art will recognize which solvates or inclusion complexes are acceptable to be used in subsequent biological assays. It is to be understood that the specific form (e.g., salt, free base, solvate, inclusion complex) of a compound of the present disclosure as isolated as described herein is not necessarily the only form in which said compound can be applied to a biological assay in order to quantify the specific biological activity.

One aspect of the disclosure is salts of the collected medication according to the disclosure including all inorganic and organic salts, especially all pharmaceutically acceptable inorganic and organic salts, particularly all pharmaceutically acceptable inorganic and organic salts customarily used in pharmacy.

It is a further object of the disclosure to provide collected medications disclosed herein, methods of purifying the medications well established in the art, and methods of using the purified medications for treating of a disease in a subject in a subject thereof.

As used herein, "treating" means administering to a subject a pharmaceutical composition to ameliorate, reduce, lessen or eliminate the symptoms of a disease, condition, deficiency, disorder or the disease itself. As used herein, "treating" or "treat" describes the management and care of a subject for the purpose of combating or eliminating a disease, condition, deficiency or disorder and includes the administration of a compound disclosed herein, or a pharmaceutically acceptable salt, polymorph or solvate thereof, to alleviate the symptoms or complications of a disease, condition or disorder, or to eliminate the disease, condition or disorder. The term "treat" may also include treatment of a cell in vitro or an animal model. As used herein, "subject" or "subjects" refers to any animal, not limiting examples include mammals such as rodents (e.g., mice or rats), dogs, primates, lemurs or humans.

Treating diseases may result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating diseases may result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating diseases may result in a decrease in the mortality rate of a population of treated subjects in comparison to a population receiving carrier alone. Treating cancer may result in a decrease in the mortality rate of a population of treated subjects in comparison to an untreated population. Treating diseases may result in a decrease in the mortality rate of a population of treated subjects in comparison to a population receiving no therapy, or monotherapy with a drug that is not a compound disclosed herein, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

REFERENCES

1. Taubenberger J K, Morens D M (January 2006). "1918 Influenza: the mother of all pandemics". Emerging Infectious Diseases. 12 (1): 15-22. doi:10.3201/eid1201.050979. PMC 3291398. PMID 16494711.
2. available at: reuters.com/article/flu-greece/greece-bans-anti-flu-drug-exports-idUSL1380811200090501
3. available at: nytimes.com/2020/02/28/health/drug-coronavirus-shortage.html
4. available at: thehill.com/changing-America/well-being/prevention-cures/485216-first-coronavirus-related-drug-shortage-hits-us
5. available at: cnbc.com/2020/02/28/fda-reports-first-coronavirus-related-drug-shortage.html
6. available at: snopes.com/ap/2020/02/28/us-reports-first-drug-shortage-tied-to-coronavirus-outbreak/
7. available at: uschamber.com/how-much-tamiflu-us-government-stockpiling
8. available at: fda.gov/media/77829/download
9. available at: ncbi.nlm.nih.gov/pubmed/10429835
10. available at: ncbi.nlm.nih.gov/books/NBK547844/
11. available at: accessdata.fda.gov/drugsatfda_docs/label/2006/020634s040, 020635s043,021721s0071bl.pdf
12. available at: glowm.com/resources/glowm/cd/pages/drugs/c048.html
13. available at: fda.gov/media/75526/download
14. available at: ncbi.nlm.nih.gov/pubmed/32074550
15. A Method for the recovery of penicillin from the urine, Lawrence Sophian M D. J. Lab and Clin Med, St. Louis, 29:769-771, July 1944. US Marine Hospital, Staten Island, N.Y. (available at: https://ia801600.us.archive.org/7/items/in.ernet.dli.2015.116336/2015.116336. The-Journal-Of-Laboratory-And-Clinical-Medicine29.pdf)
16. available at: accessdata.fda.gov/drugsatfda_docs/label/2007/021226s0221bl.pdf
17. available at: foxnews.com/world/chinese-deny-americans-coronavirus-drugs

What is claimed is:

1. A non-invasive, non-gravitationally dependent, pressurized filtration method to selectively reclaim at least one medication from urine, comprising:
   (a) collecting urine containing at least one medication from at least one subject;
   (b) passing said urine through a non-gravitationally dependent pressurized filtration system comprising:
      (i) a source of pressurization;
      (ii) a first mesh or filter configured to prevent the passage of components in urine that have a size greater than about 1 kilodalton while permitting passage of smaller components; and
(iii) a second mesh or filter configured to allow passage of effluent from the first mesh or filter while preventing passage of the at least one medication dissolved in the effluent;
whereby the source of pressurization propels the urine through the first and second mesh or filter, and wherein the bacteria/cells, contaminants, toxins, and liquid waste are removed/separated by the pressurized filtration system, and the at least one medication is trapped in the pressurized filtration system; and
(c) collecting the at least one medication from the pressurized filtration system, wherein collecting the at least one medication from the pressurized filtration system does not comprise chromatography.

2. The method of claim 1, wherein (b) comprises passing said urine through the first mesh or filter, and directing the effluent from the first mesh or filter through the second mesh or filter, wherein the at least one medication is retained by the second mesh or filter while the liquid or liquid waste passes through the second mesh filter as effluent.

3. The method of claim 1, wherein the pressurized filtration method is integrated into, designed into, manufactured as a part of, adapted to work with, engineered into a water reclamation system, thereby enabling said water reclamation system to gain the functionality of reclaiming at least one medication from urine, without interfering with the original function(s) of the water reclamation system.

4. The method of claim 1, wherein the effluent which passes through the second mesh or filter is stored.

5. The method of claim 1, wherein the first mesh or filter and the second mesh or filter are in fluid connection to one another as a single unit or via a connector.

6. The method of claim 1, wherein:
(a) the first mesh or filter comprises at least one mesh or filter selected from the group consisting of a microfiltration system, an ultrafiltration system, mesh, reverse osmosis, forward osmosis, and a nanofiltration system, and is configured to prevent passage of urine components selected from the group consisting of suspended solids, bacteria, cells, fats, enzymes, oils, viruses, proteins, macromolecules, and combinations thereof; and
(b) the second mesh or filter comprises at least one mesh or filter selected from the group consisting of reverse osmosis filtration system, forward osmosis system and a nanofiltration system, wherein the reverse osmosis filtration, forward osmosis filtration system and/or nanofiltration system is configured such that pressurization of the system propels the urine to pass through the second mesh or filter as effluent while trapping the at least one medication in or on the second mesh or filter.

7. The method of claim 1, wherein the urine is from a mammal.

8. The method of claim 1, wherein the at least one subject:
(a) is taking only one medication; or
(b) is taking multiple medications, but any medication(s) not being recovered are either not excreted in urine, are not recovered from urine in active form, and/or can be separated/processed out from a desired medication(s).

9. The method of claim 1, wherein the at least one medication is selected from the group consisting of: antibiotics; antivirals; antifungals; steroids; antimicrobial; antiparasitic; vitamins; proteins; and supplements; wherein the at least one medication is contained in the urine in an unchanged, active, inactive, or recoverable form in clinically significant amounts.

10. The method of claim 1, further comprising testing the medication reclaimed from the pressurized filtration system for purity or concentration, optionally sterilizing the medication, and optionally reusing or storing the medication.

11. The method according to claim 1, wherein the at least one medication comprises naturally occurring or engineered hormones, chemicals, antibodies, lipids, proteins, enzymes, or pharmaceutical products.

12. The method according to claim 1, wherein the source of pressurization is selected from the group consisting of: compressed air, compressed gas, tank, a pump, a motor, and a compressor.

13. The method of claim 1, wherein the source of pressurization is human-powered, mechanical, electrical, hydraulic, or pneumatic.

* * * * *